United States Patent [19]
Peacock, III et al.

[11] Patent Number: 6,059,770
[45] Date of Patent: May 9, 2000

[54] CATHETER PROVIDING INTRALUMINAL ACCESS

[75] Inventors: James C. Peacock, III, Corona Del Mar; Richard J. Saunders, Redwood City, both of Calif.

[73] Assignee: Advanced Cardiovascular Systems, Inc., Santa Clara, Calif.

[21] Appl. No.: 08/984,014

[22] Filed: Dec. 3, 1997

Related U.S. Application Data

[62] Division of application No. 08/805,896, Feb. 24, 1997, Pat. No. 5,902,290, which is a continuation of application No. 08/589,910, Jan. 23, 1996, abandoned, which is a continuation of application No. 08/212,225, Mar. 14, 1994, abandoned.

[51] Int. Cl.$^7$ .................................................. A61M 25/00
[52] U.S. Cl. ............................................. 604/526; 604/264
[58] Field of Search ................................... 604/264, 280, 604/282, 523, 524, 526; 128/585

[56] References Cited

U.S. PATENT DOCUMENTS

| | | |
|---|---|---|
| 3,938,529 | 2/1976 | Gibbons . |
| 4,516,972 | 5/1985 | Samson ................... 604/282 |
| 4,581,017 | 4/1986 | Sahota . |
| 4,737,153 | 4/1988 | Shimamura et al. . |
| 4,739,768 | 4/1988 | Engelson . |
| 4,932,413 | 6/1990 | Shockey et al. . |
| 4,944,740 | 7/1990 | Buchbinder et al. . |
| 4,947,864 | 8/1990 | Shockey et al. . |
| 4,976,689 | 12/1990 | Buchbinder et al. . |
| 5,120,323 | 6/1992 | Shockey et al. . |
| 5,163,921 | 11/1992 | Feiring . |
| 5,195,971 | 3/1993 | Sirhan ....................... 604/96 |
| 5,201,723 | 4/1993 | Quinn . |
| 5,234,003 | 8/1993 | Hall ........................ 600/585 |
| 5,246,421 | 9/1993 | Saab . |
| 5,257,974 | 11/1993 | Cox . |
| 5,279,562 | 1/1994 | Sirhan et al. .............. 604/96 |
| 5,279,596 | 1/1994 | Casteneda et al. . |
| 5,290,230 | 3/1994 | Ainsworth et al. ......... 604/96 |
| 5,318,535 | 6/1994 | Miraki . |
| 5,328,472 | 7/1994 | Steinke et al. . |
| 5,344,402 | 9/1994 | Crocker .................... 604/96 |
| 5,380,304 | 1/1995 | Parker . |
| 5,383,890 | 1/1995 | Miraki et al. .............. 606/194 |
| 5,460,608 | 10/1995 | Lodin et al. ............... 604/96 |
| 5,542,925 | 8/1996 | Orth ......................... 604/102 |
| 5,554,114 | 9/1996 | Wallace et al. ............ 604/53 |
| 5,573,509 | 11/1996 | Thornton ................... 604/102 |
| 5,591,129 | 1/1997 | Shoup et al. .............. 604/96 |
| 5,630,806 | 5/1997 | Inagaki et al. ............ 604/282 |

FOREIGN PATENT DOCUMENTS

| | | |
|---|---|---|
| 0 439 032 A-1 | 12/1990 | European Pat. Off. . |
| WO 93/01856 | 2/1993 | WIPO . |
| WO 93/13826 | 7/1993 | WIPO . |
| WO 93/21985 | 11/1993 | WIPO . |

OTHER PUBLICATIONS

Michael B. Selig, M.D., "Lesion Protection During Fixed–Wire Balloon Angioplasty: Use of 'Buddy Wire' Technique and Access Catheters," Catheterization and Cardiovascular Diagnosis 25:331–225 (1992).

*Primary Examiner*—Corrine McDermott
*Attorney, Agent, or Firm*—Heller Ehrman White & McAuliffe

[57] ABSTRACT

An intraluminal catheter which provides access to distal locations within a patient's body lumen and which is provided with a flexible distal section having an inner lining, an outer jacket or coating and a helical coil between the lining and jacket. The distal section of the catheter is quite flexible yet it has sufficient transverse or radial rigidity to prevent significant distortion of the transverse cross-sectional shape of the catheter.

11 Claims, 3 Drawing Sheets

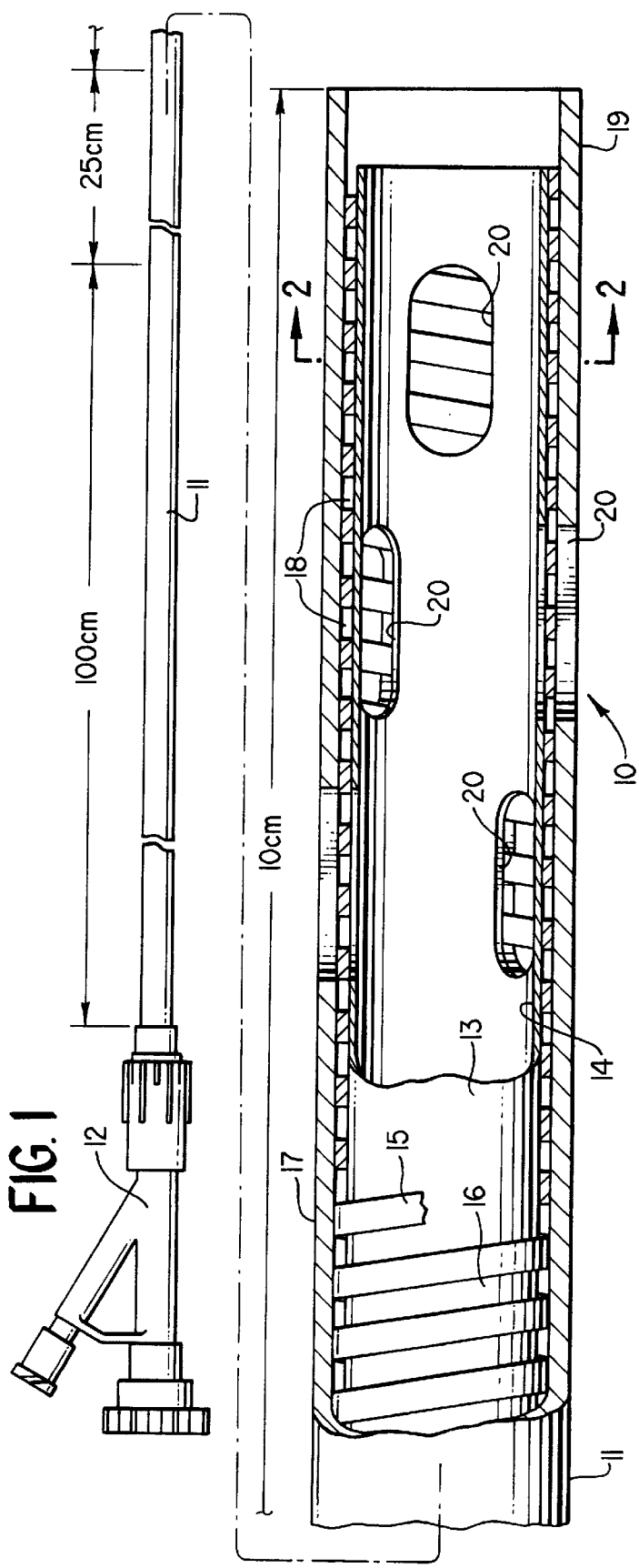

CATHETER PROVIDING INTRALUMINAL ACCESS

This is a divisional application of application Ser. No. 08/805,896, which was filed on Feb. 24, 1997, now U.S. Pat. No. 5,902,290, which is a continuation of application Ser. No. 08/589,970 filed Jan. 23, 1996, now abandoned, which is a continuation of application Ser. No. 08/212,225, filed Mar. 14, 1994, now abandoned.

FIELD OF THE INVENTION

This invention generally relates to intraluminal access catheters which are adapted to facilitate the advancement and withdrawal of intraluminal devices such as balloon dilatation catheters, guidewires and the like used in percutaneous transluminal coronary angioplasty (PTCA) procedures.

BACKGROUND OF THE INVENTION

In typical PTCA procedures, a guiding catheter having a preshaped distal tip is percutaneously introduced by a Seldinger technique into the cardiovascular system of a patient and advanced within the system until the preshaped distal tip of the guiding catheter is disposed within the ascending aorta adjacent the ostium of the desired coronary artery. The guiding catheter is relatively stiff because it has to be twisted or torqued from its proximal end, which extends outside the patient, to turn the distal tip of the guiding catheter so that it can be guided into the desired coronary ostium. A balloon dilatation catheter is introduced into and advanced through the guiding catheter and out the distal tip thereof into the patient's coronary artery until the balloon on the distal extremity of the dilatation catheter is properly positioned across the lesion to be dilated. Once properly positioned, the balloon is inflated one or more times to a predetermined size with radiopaque liquid at relatively high pressures (e.g., generally 4–12 atmospheres) to dilate the stenotic region of the diseased artery. When the dilatations have been completed, the balloon is finally deflated so that the dilatation catheter can be removed from the dilated stenosis to allow the resumption of normal blood flow through the dilated artery.

There are several types of balloon dilatation catheters which are now widely available, including over-the-wire catheters, fixed-wire catheters, rapid exchange type catheters (which are a type of over-the-wire catheter) and perfusion type catheters (which may be either over-the-wire or fixed-wire catheters).

It is not uncommon during an angioplasty procedure to have to exchange the dilatation catheter once the dilatation catheter has been advanced within the patient's coronary artery. For example, if the physician determines that the inflated balloon size of the catheter is inappropriate for the stenosis to be dilated, the dilatation catheter will be withdrawn and an appropriately sized dilatation catheter will be advanced into the coronary artery to dilate the stenosis.

If the dilatation catheter employed is an over-the-wire type dilatation catheter, the catheter may be withdrawn from the patient with the guidewire remaining in place across the stenosis to be dilated so that access to this stenotic region is not lost. It should be noted that it may take the physician from about 15 minutes to up to two hours or more to first advance the guidewire into the patient's coronary artery and across the stenosis to be dilated and then advance the distal portion of the dilatation catheter having the balloon across the stenotic region.

However, when a fixed-wire dilatation catheter is withdrawn from the patient's coronary artery, in order to exchange the catheter for another sized fixed-wire catheter or another type catheter, access to the stenotic region is lost. It may take the physician an hour or more to advance a replacement fixed-wire catheter or a guidewire over which an over-the-wire dilatation catheter can be advanced through the patient's tortuous coronary anatomy in order to reach the arterial stenotic region in which the first fixed-wire dilatation catheter was located.

Exchange type catheters are described in U.S. Pat. No. 4,944,740 and U.S. Pat. No. 4,976,689 which are designed to facilitate the advancement and withdrawal of fixed-wire devices within a patient's coronary arteries without loss of access to the stenotic region. However, the commercial embodiments of these patents has been found to be relatively ineffective when they are advanced through highly tortuous coronary arteries and when using guiding catheters with small radii of curvatures, i.e. tight curvatures, such as found in guiding catheters having Amplatz configurations. Commercially available exchange type catheters have a tendency to collapse or kink when advanced through tight curvatures, thereby preventing the passage of the fixed-wire or other type of intravascular catheter through the inner lumen of the exchange catheter. In some instances the change in transverse cross-sectional shape of the inner lumen of commercially available exchange catheters from circular to oval shaped is sufficient to prevent or retard the passage of a dilatation catheter or guidewire through the exchange catheter.

What has been needed and heretofore unavailable is an exchange type catheter having a highly flexible distal end which has sufficient radial rigidity to maintain the cross-sectional shape of the inner lumen when the distal end is in a configuration with a small radius of curvature. The present invention satisfies that and other needs.

SUMMARY OF THE INVENTION

The present invention is directed to an improved intraluminal access catheter which is particularly suitable for facilitating the advancement and the withdrawal of intravascular devices such as fixed-wire and other types of dilatation catheters, guidewires and the like through a patient's coronary arteries.

The access catheter of the invention has an elongated proximal portion, a relatively short distal portion and an inner lumen extending therethrough which is adapted to facilitate the passage therethrough of guidewires, fixed-wire and over-the-wire dilatation catheter and other intravascular devices. The proximal portion of the catheter is sufficiently stiff to facilitate advancing the catheter through a guiding catheter and a patient's coronary artery. The distal portion is longitudinally flexible enough so as to be readily advanced through guiding catheters having distal ends with tight curvatures and tortuous coronary anatomy and it has sufficient radial rigidity so that the transverse cross-sectional shape of the inner lumen which extends through the distal portion is maintained even when the distal portion of the catheter is put into a configuration with one or more tight curvatures.

The flexible distal portion of the access catheter, which is dimensioned to be advanced through the a human patient's coronary artery, generally has a tubular shape and comprises an inner lining defining the inner lumen extending therethrough, which preferably has an inner lubricous surface, an outer plastic jacket and a supporting coil disposed between the inner tubular lining and an outer jacket. The supporting coil is a self supporting tubular structure and may be a singular, helically wound coil or a two or more strands which have been braided. A helically wound coil is preferred in order to provide a greater degree of flexibility to the distal portion of the catheter shaft. The plastic jacket and the inner tubular lining may be formed of separate materials and secured together with the coil therebetween by means of a suitable adhesive or they may be formed of separate tubes of the same material and formed into a unitary construction by heat bonding the outer jacket and the inner tubular lining together with the helical coil disposed between the tubular members. Other means of forming the exchange catheter of the invention are contemplated, such as coextruding the inner tubular lining and the outer jacket from the same or similar polymeric materials about the coil and heat forming the extruded tubular member to bond the components together into the catheter shaft after the extruding procedures.

The polymer material from which the outer jacket on the distal portion of the exchange catheter is made is a thermoplastic polymer which is preferably selected from the group consisting of polyurethane, polyethylene, polyvinyl chloride, polypropylene, polyamide and the like. Preferably, the cured polymer jacket on the distal end should have durometer hardness (Shore) of about 90A to about 55D. The diameter of the inner lumen extending through the exchange catheter should range from about 0.008 to about 0.06 inch in order to accommodate various sizes of dilatation catheters. Several different sized access catheters can be offered to handle the entire size range of available dilatation catheters, guidewires and other intravascular devices.

In one presently preferred embodiment the access catheter is provided with one or more perfusion ports in the wall of the distal portion of the access catheter so that oxygenated blood can pass into the interior lumen of the exchange catheter at a proximal location on the distal portion of the catheter and then out of the distal portion of the catheter at various locations along its length which may be both proximal and distal to the stenotic region of the patient's artery which is to be dilated.

In another presently preferred embodiment the access catheter is provided with a distal guidewire port located in the distal end of the catheter and a proximal guidewire port spaced a short distance, e.g. at least about 5 cm, and preferably at least about 10 cm, from the distal port and a substantial distance, e.g. about 80 to about 120 cm, from the proximal end of the exchange catheter. Both guidewire ports are in communication with the inner lumen which extends through the distal portion of the catheter.

In use, the access catheter of the invention is advanced over a guidewire or fixed-wire dilatation catheter which has been previously positioned within the patient's coronary artery until the distal end of the access catheter extends to a location adjacent to or within the stenosed arterial region. In the case of the fixed wire catheters, the adapter must be removed in order to advance the access catheter over the in-place fixed wire catheter. The adapter may be a removable adapter or it may be severed from the proximal end of the catheter. The guidewire or fixed-wire dilatation catheter may then be withdrawn through the inner lumen of the access catheter while maintaining the position of the distal end of the access catheter at or near the location of the distal end of the guidewire or fixed-wire catheter prior to the withdrawal thereof. A replacement fixed-wire dilatation catheter, guidewire, or other device, can be readily advanced through the inner lumen of the access catheter.

There is little tendency for the catheter or guidewire which is advanced or withdrawn through the inner lumen of the access catheter of the invention to become bound-up within the inner lumen because the transverse cross-sectional shape of the inner lumen remains essentially circular when the access catheter, particularly the distal portion thereof, is configured into a curvature with a small radius of curvature, e.g. about 1 cm and even as small as about 0.5 cm, which may occur when the access catheter passes through the distal end of a guiding catheter with an Amplatz shape or when passing through tortuous coronary anatomy.

These and other advantages of the invention will become more apparent from the following detailed description thereof, when taken in conjunction with the accompanying exemplary drawings.

BRIEF DESCRIPTION OF THE DRAWINGS

FIG. 1 is a longitudinal view, partially in section, of an exchange catheter embodying features of the invention.

FIG. 2 is a transverse cross-sectional view of the exchange catheter shown in FIG. 1 taken along the lines 2—2.

DETAILED DESCRIPTION OF THE INVENTION

Figure 3:
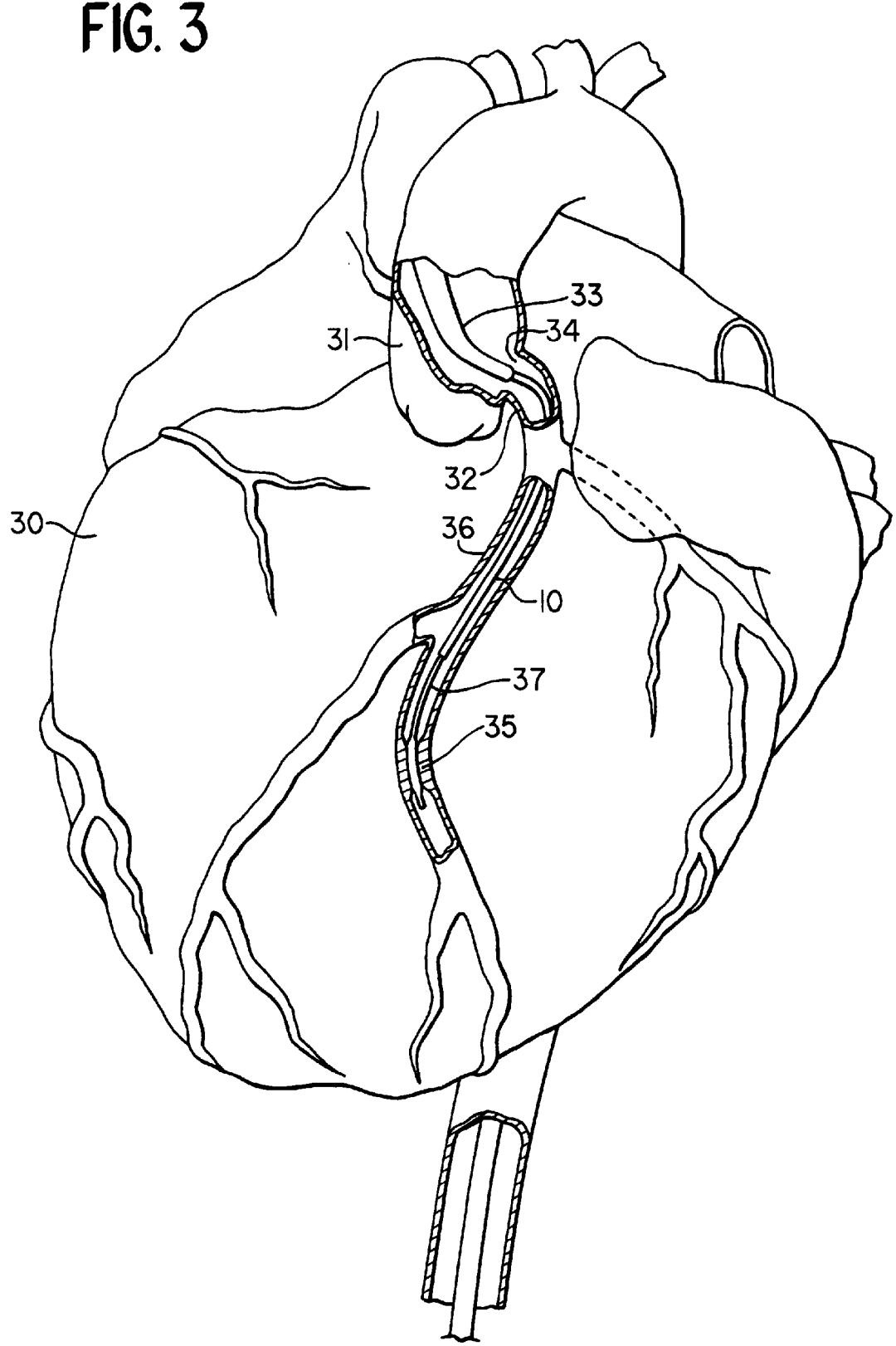
FIG. 3 is schematic elevational view of a human heart with the left coronary artery partially cut-away demonstrating a stenosis in the left anterior diagonal artery.

FIGS. 1 and 2 depict an access catheter 10 embodying features of the invention which generally includes an elongated catheter shaft 11 and an adapter 12 on the proximal end of the catheter. The catheter shaft 11 includes an inner tubular lining 13 which preferably has a lubricous inner surface defining an inner lumen 14, a helical coil 15 about the inner tubular lining which is stretched or longitudinally expanded at least in its distal portion to provide spaces 16 between individual turns of the coil, and an outer jacket 17. The jacket 17 and the inner tubular lining 13 are bonded together by means of an adhesive 18 which is disposed in the spaces 16 between the turns of the coil 15. Alternatively the jacket 17 and inner tubular lining 13 may be joined together by heat bonding wherein the material thereof flows between the turns of the coil 15. The distal end of the coil 15 terminates short of the distal end of the catheter shaft 11 and a relatively soft, non-traumatic distal tip 19 extends beyond the distal ends of the coil 15 and the inner lining 13. The non-traumatic tip 19 may be an extension of the jacket 17 as shown and may also be tapered.

The distal portion of the catheter shaft 11 is provided with perfusion ports 20 extending along a length of the catheter shaft which is to be disposed within the patient's coronary artery, e.g. about 5 to about 40 cm. These perfusion ports are conveniently formed by a $CO_2$ laser which selectively burns away the jacket 17, the inner tubular lining 13 and the adhesive 18 which secures these two members together but does not significantly affect the helical metallic coil 15. While a plurality of perfusion ports along the length of the distal portion of the catheter shaft 11 are shown in the drawing, one elongated perfusion port could be employed to replace a plurality of such ports. Moreover, perfusion ports may be provided disposed at various angles from one another. Additionally, they may be spirally arranged about the periphery of the catheter shaft 11. Generally, perfusion ports, guidewire ports and the like may be formed by means of a CO, $CO_2$ or Eximer laser with an emitting light having a wave length of about 0.1 to about 12 microns will preferentially burn off the plastic material but will not affect metallic supporting elements such as the coil or braid of the present invention. If desired, e.g. to improve blood flow, other types of lasers with emitting light with shorter wavelengths or other means may be employed to remove portions of the metallic coil 15 which are exposed by perfusion or guidewire ports.

Figure 6:
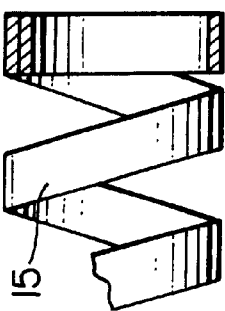
FIG. 6 is an enlarged view, partially in section, of a supporting coil which embodies features of the invention.

The materials of construction may be conventional. The jacket 17 may be a suitable thermoplastic polymer such as polyurethane, polyethylene, polyvinyl chloride and the like. The exterior of the jacket 17 may be provided with a lubricous coating such as a polysiloxane or suitable hydrophilic material. The inner tubular 13 member may be formed of a fluoropolymer to provide lubricity to the inner surface thereof which forms the inner lumen 14. In the alternative, the inner tubular member may be formed of a thermoplastic polymer and the inner surface of the inner tubular member defining the inner lumen 14 may be provided with a lubricous coating as describe above for the exterior of the jacket 17. The helical coil 15 may be in form of a wire or ribbon and may be formed of 304 stainless steel or a superelastic nickel-titanium alloy which is frequently identified by the acronym NITINOL (Nickel-Titanium Naval Ordnance Laboratory) or a high strength plastic material. A particularly suitable superelastic NITINOL is described in copending application Ser. No. 07/629,381, filed Dec. 18, 1990 entitled Superelastic Guiding Member which is incorporated by reference herein in its entirety. The free distal tip of the coil 15 is preferably joined, e.g. by laser welding or a suitable adhesive to an adjacent turn of the coil, as shown in FIG. 6, so as to preclude the possibility that the tip penetrate through the wall of the catheter and damage the artery through which the catheter is advanced. The laser welding may be preferred in view of ease of use, the high strength bonds which result and the small bond areas required.

Figure 4:
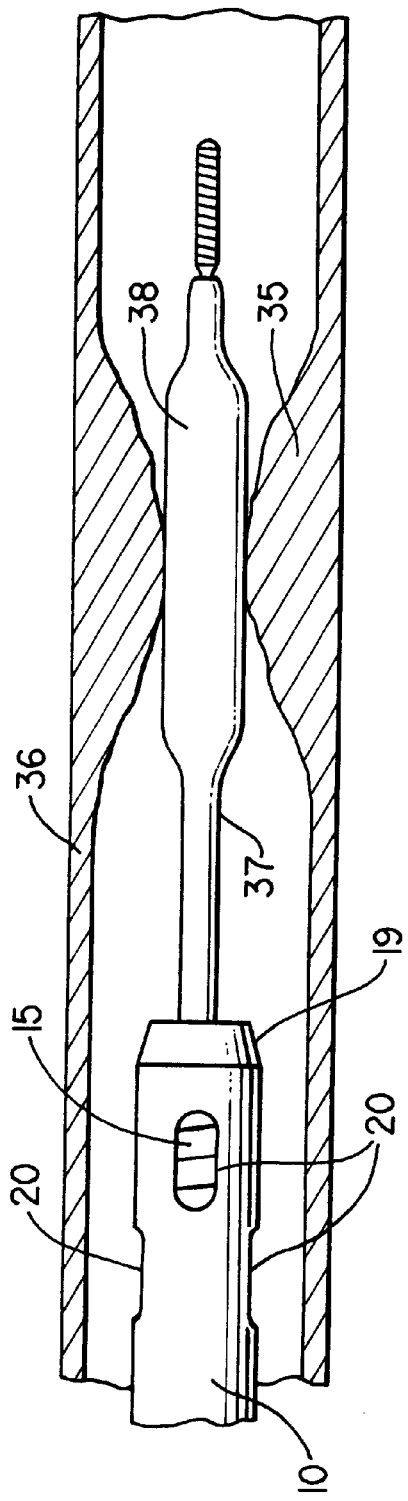
FIG. 4 is an enlarged view of the stenotic region shown in FIG. 3.

One presently preferred use of the access catheter 10 is illustrated in conjunction with FIGS. 3 and 4 which schematically illustrates a human heart 30 with portions of the ascending aorta 31 and the left coronary artery 32 cut away to show the guiding catheter 33 and the access catheter of the invention disposed therein. The distal portion of the guiding catheter 33 is disposed within the ascending aorta 31 with the distal tip thereof extending within the ostium 34. The access catheter 10 extends out the distal end of the guiding catheter 33 into the left coronary artery 32 of the patient to a location proximal to the stenotic site 35 in the left anterior diagonal branch 36.

A fixed-wire balloon dilatation catheter 37 is advanced out the distal end of the exchange catheter 10 over with the balloon 38 of the dilatation catheter extending across the stenosis 35. The balloon 38 is inflated one or more times to dilate the stenosis 35. If the dilatation catheter 37 needs to be exchanged, e.g. if the inflated diameter of the balloon 37 is insufficient to completely dilate the stenosis 35, it is withdrawn from the patient and a replacement dilatation catheter is advanced through the access catheter 10 to cross then dilate the stenosis 35.

The access catheter is also useful in facilitating the advancement of a variety of catheters and elongated intravascular devices through a tight passageway such as a lesion by increasing the support and thus the pushability of the catheter or device.

In order for the access catheter to be advanced through a guiding catheter and out into a patient's coronary artery, the overall length of the access catheter must be longer, preferably at least about 5 cm longer than the guiding catheter used and at least about 2 cm shorter than the dilatation catheter or guidewire used. To facilitate the advancement of the access catheter through the inner lumen of the guiding catheter, the outer diameter of the access catheter must be smaller, preferably at least about 0.005 inch (0.127 mm) smaller, than the inner diameter of the guiding catheter. The inner diameter of the access catheter must be of sufficient size to allow a balloon dilatation catheter or other catheter or elongated device, which is to be used to perform the intravascular procedure, to be slidably advanced through the inner lumen of the access catheter. Typically, commercially available guiding catheters have lengths of about 100 cm, outer diameters at the distal extremity thereof of about 2.3 to about 2.6 mm and inner diameters at the distal extremity of about 1.5 to about 2.2 mm. Commercially available balloon dilatation catheters typically have lengths of about 135 cm and have a shaft outer diameter generally ranging from about 0.5 to about 1.3 mm. Commercially available guidewires typically have lengths of about 175 cm and diameters ranging from about 0.01 to about 0.018 inch (0.25–0.46 mm).

In a presently preferred embodiment of the invention the catheter jacket is formed of polymers which provide a variable cured hardness along the length of the catheter shaft with the most proximal portion of the catheter shaft of about 70 to about 100 cm in length having a hardness of about 40 to about 90D Shore hardness and a distal section having a hardness of about 60 to about 100A Shore hardness. An intermediate section may be added with an intermediate hardness between the hardness of the proximal and distal sections.

Figure 5:
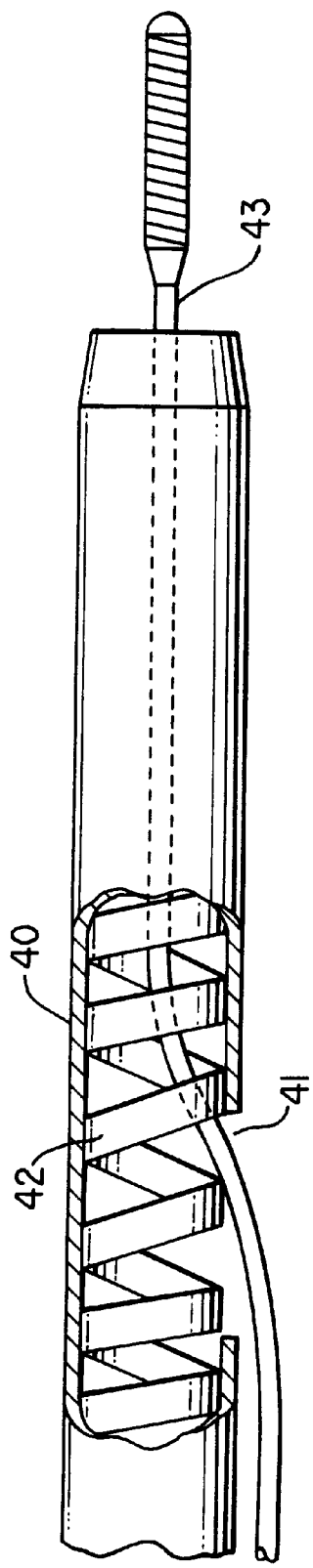
FIG. 5 is an elevational view, partially in section, of the distal portion of an alternative embodiment of the invention with rapid exchange capabilities.

FIG. 5 illustrates an alternative embodiment of the access catheter 40 of the invention in a rapid exchange design which has a guidewire port 41 spaced a short distance, e.g. at least about 5 cm and preferably at least about 10 cm from the distal end of the catheter and a substantial distance from the proximal end of the catheter. The helical supporting coil 42 is longitudinally expanded a greater distance than the coil 15 shown in the previously discussed embodiment in the region of the proximal guidewire port 41 in order to accommodate the passage of the guidewire 43 through the port 41. This embodiment may also be provided with perfusion ports (not shown) as in the previously discussed embodiment which are disposed between the proximal guidewire port 41 and the distal end of the catheter 40. The helical coil 42 may extend just through the distal portion of the catheter 40 with the proximal extension of the coil terminating distal to the guidewire port 41.

Progressively smaller diameter guiding catheters have been used in angioplasty, atherectomy and other intra coronary procedures over the years with the result that there has been less room within the inner lumen of the guiding catheters for delivery of radiopaque and other fluid through the inner lumen and out the distal end of the guiding catheter. Higher fluid pressure is required for effective delivery of the fluid. With the catheter of the present invention this effect can be minimized by extending the ports in the wall of the catheter along its length which is to be disposed within the inner lumen of the guiding catheter. In this manner the radiopaque fluid or for that matter any fluid which is introduced under pressure into the guiding catheter, will enter into the inner lumen of the catheter of the invention through the ports in the wall and flow through the inner lumen and out the distal end thereof, thus allowing a greater overall fluid flow through the guiding catheter.

While the present invention has been described herein in terms of certain preferred embodiments, diverted to a catheter which is used to give access to distal locations within a patient's coronary anatomy, those skilled in the art will recognize that, a variety of modifications and improvements can be made to the invention without departing from the scope thereof.

What is claimed is:

1. An assembly for performing an angioplasty procedure within a patient's coronary artery, comprising:
   a) an elongated guiding catheter having a proximal end with a port therein and a distal end with a port therein and an inner lumen extending within the catheter between the ports provided in the proximal and distal ends; and
   b) an access catheter slidably disposed within the inner lumen of the guiding catheter which comprises:
      an elongated catheter shaft having proximal and distal ends a distal tip and a port in the distal tip;
      an inner lumen which extends therein to the port in the distal tip of the catheter shaft; and
      a flexible distal section of the elongated catheter shaft which is formed of a tubular member and a longitudinally expanded helical supporting coil within the tubular member, with at least one opening in a wall portion of the tubular member which exposes at least part of one turn of the expanded helical supporting coil and space between said turn and an adjacent turn which provides fluid communication from outside the catheter shaft to the inner lumen of the access catheter shaft.

2. The catheter of claim 1 wherein the access catheter shaft has at least one port in a proximal portion thereof which is adapted to remain within the guiding catheter.

3. The assembly of claim 1 wherein the elongated catheter shaft of the access catheter has a length which is at least 5 cm greater than the length of the guiding catheter.

4. The assembly of claim 1 wherein the elongated catheter shaft of the access catheter has an outer diameter less than the inner lumen of the guiding catheter.

5. The assembly of claim 1 wherein the elongated catheter shaft of the access catheter has an outer diameter of at least about 0.005 inch smaller than the inner lumen of the guiding catheter.

6. An assembly for performing an angioplasty procedure within a patient's coronary artery, comprising:
   a) an elongated dilatation catheter having a catheter shaft with an inflatable dilatation member on a distal portion of the catheter shaft; and
   b) an access catheter which comprises:
      an elongated catheter shaft having proximal and distal ends, a distal tip and a port in the distal tip;
      an inner lumen which extends therein to the port in the distal tip of the catheter shaft and the dilatation catheter slidably disposed therein;
      a flexible distal section of the elongated catheter shaft which is formed of a tubular member and a longitudinally expanded helical supporting coil within the tubular member, with at least one opening in a wall portion of the tubular member which exposes at least part of one turn of the expanded helical supporting coil and space between said turn and an adjacent turn which provides fluid communication form outside the catheter shaft to the inner lumen of the access catheter shaft.

7. The assembly of claim 6 wherein the access catheter is at least 2 cm shorter than the dilatation catheter.

8. The assembly of claim 6 wherein the dilatation catheter is a fixed-wire dilatation catheter.

9. The assembly of claim 8 wherein the fixed-wire dilatation catheter has proximal end with a removable adapter thereon.

10. An assembly for performing an intravascular procedure within a patient's coronary artery, comprising:
    a) an elongated guidewire having an elongated core member with a flexible coil member on a distal portion of the guidewire; and
    b) an access catheter which comprises:
       an elongated catheter shaft having proximal and distal ends, a distal tip, and a port in the distal tip;
       an inner lumen which extends therein to the port in the distal tip of the catheter shaft and the guidewire slidably disposed therein;
       a flexible distal section of the elongated catheter shaft formed of a tubular member and a longitudinally expanded helical supporting coil within the tubular member, with at least one opening in a wall portion of the tubular member which exposes at least part of one turn of the expanded helical supporting coil and space between said turn and an adjacent turn which provides fluid communication from outside the catheter shaft to the inner lumen of the access catheter shaft.

11. The assembly of claim 10 wherein the access catheter is at least 5 cm shorter than the guidewire.

* * * * *